United States Patent
Ruben et al.

[11] Patent Number: 5,885,471
[45] Date of Patent: Mar. 23, 1999

[54] SHOCK RESISTANT ACCELEROMETER FOR IMPLANTABLE MEDICAL DEVICE

[75] Inventors: David A. Ruben, Mesa; Mark E. Henschel, Phoenix; Larry R. Larson, Chandler; Roy Inman, Phoenix; Louis A. Molinari, Chandler; Joan A. O'Gara; Ronald F. Messer, both of Phoenix, all of Ariz.

[73] Assignee: Medtronic, Inc., Minneapolis, Minn.

[21] Appl. No.: 904,142

[22] Filed: Jul. 31, 1997

Related U.S. Application Data

[63] Continuation-in-part of Ser. No. 399,072, Mar. 8, 1995, Pat. No. 5,674,258.

[51] Int. Cl.$^6$ ........................................... B44C 1/22
[52] U.S. Cl. ..................... 216/33; 216/52; 128/782; 128/419 PG; 607/19; 73/517 R
[58] Field of Search ................... 216/2, 33, 52; 607/19, 17, 18, 20–26; 128/782, 419 PG; 73/514.33, 517 R

[56] References Cited

U.S. PATENT DOCUMENTS

| | | | |
|---|---|---|---|
| 4,140,132 | 2/1979 | Dahl | 128/419 PG |
| 4,379,459 | 4/1983 | Stein | 128/419 PG |
| 4,476,868 | 10/1984 | Thompson | 128/419 PG |
| 4,485,813 | 12/1984 | Anderson et al. | 128/675 |
| 4,556,063 | 12/1985 | Thompson et al. | 128/419 PT |
| 4,653,326 | 3/1987 | Danel et al. | 73/517 R |
| 4,679,434 | 7/1987 | Stewart | 73/517 B |
| 4,742,182 | 5/1988 | Fuchs | 174/52 FP |
| 4,891,985 | 1/1990 | Glenn | 73/517 R |
| 4,987,781 | 1/1991 | Reimann | 73/417 R |
| 5,014,702 | 5/1991 | Alt | 128/419 PG |
| 5,031,615 | 7/1991 | Alt | 128/419 PG |
| 5,052,388 | 10/1991 | Sivula et al. | 128/419 PG |
| 5,221,400 | 6/1993 | Staller et al. | 216/33 X |
| 5,235,237 | 8/1993 | Leonhardt | 310/329 |
| 5,309,014 | 5/1994 | Wilson | 257/584 |
| 5,312,453 | 5/1994 | Shelton et al. | 607/19 |
| 5,315,204 | 5/1994 | Park | 310/339 |
| 5,315,205 | 5/1994 | Ohno et al. | 310/357 |
| 5,318,596 | 6/1994 | Barreras et al. | 607/19 |
| 5,373,267 | 12/1994 | Kaida et al. | 333/187 |
| 5,415,726 | 5/1995 | Staller et al. | 216/33 X |
| 5,594,172 | 1/1997 | Shinohara | 73/514.33 |
| 5,595,172 | 1/1997 | Shinohara | 73/514.33 |

FOREIGN PATENT DOCUMENTS

| | | |
|---|---|---|
| 0 434 878 A1 | 7/1991 | European Pat. Off. . |
| 0 529 122 A1 | 3/1993 | European Pat. Off. . |
| 8626133 U | 6/1988 | Germany . |
| WO 91/13364 | 9/1991 | WIPO . |
| WO 95/02431 | 1/1995 | WIPO . |
| WO 95/03086 | 2/1995 | WIPO . |

*Primary Examiner*—William Powell
*Attorney, Agent, or Firm*—Thomas F. Woods; Harold R. Patton

[57] ABSTRACT

The present invention relates to accelerometer assemblies for implantable medical devices such as pacemakers, IPGs, PCDs, defibrillators, ICDs and the like. The accelerometer assembly of the present invention comprises a beam that deflects in response to being subjected to an externally provided force. Deflection of the beam generates a voltage in a piezoelectric material disposed in the assembly. At least one stop is provided to limit the vertical range of motion through which the beam may deflect to prevent failure, fracturing or breakage of the beam resulting from excessive deflection of the beam that might otherwise occur were the stop not present.

19 Claims, 16 Drawing Sheets

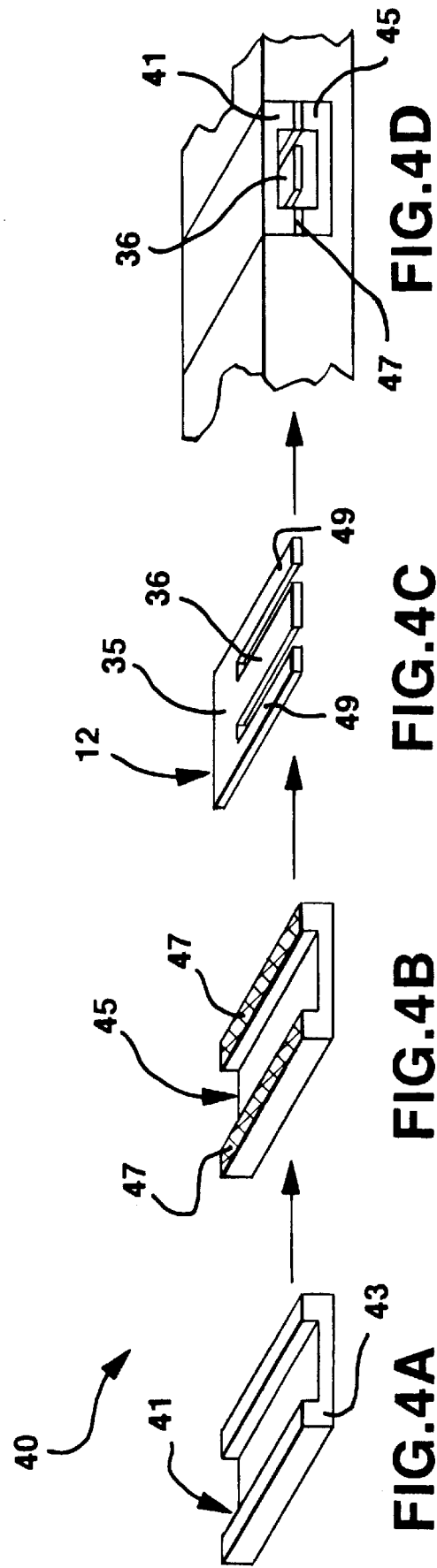

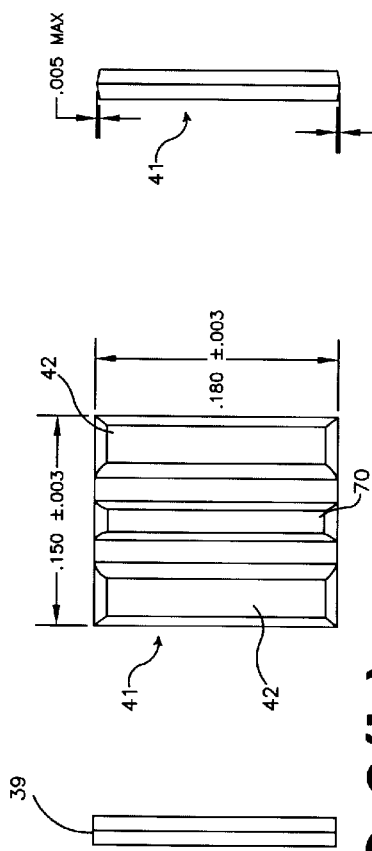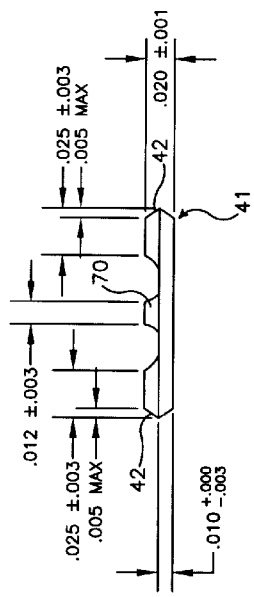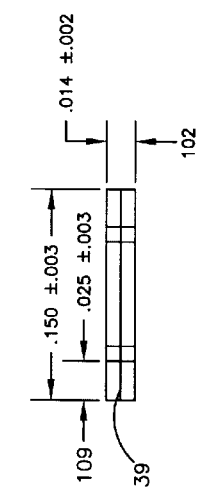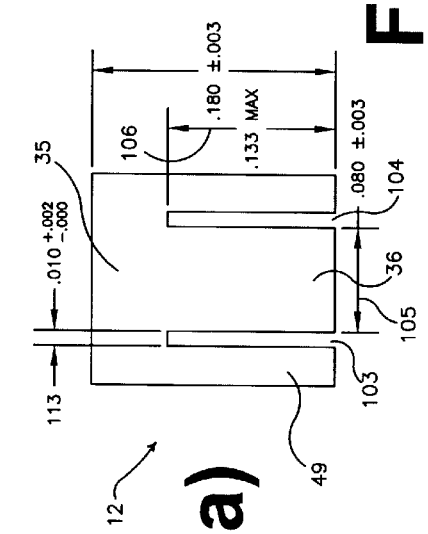

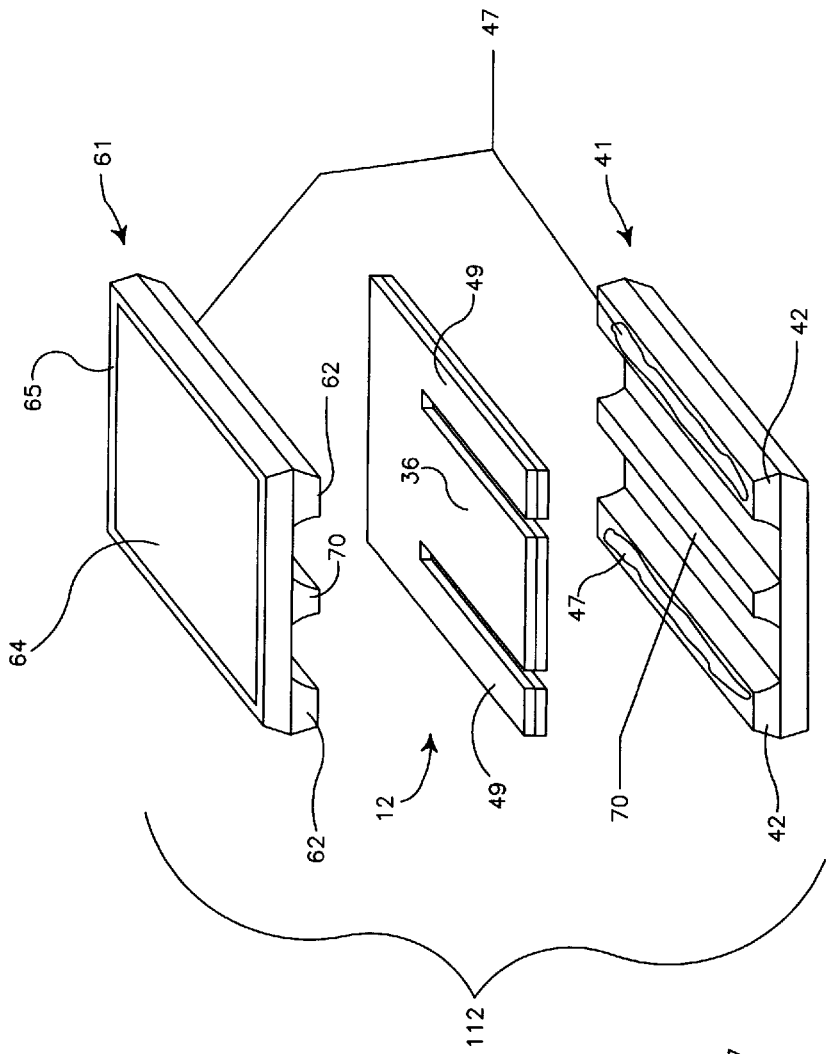
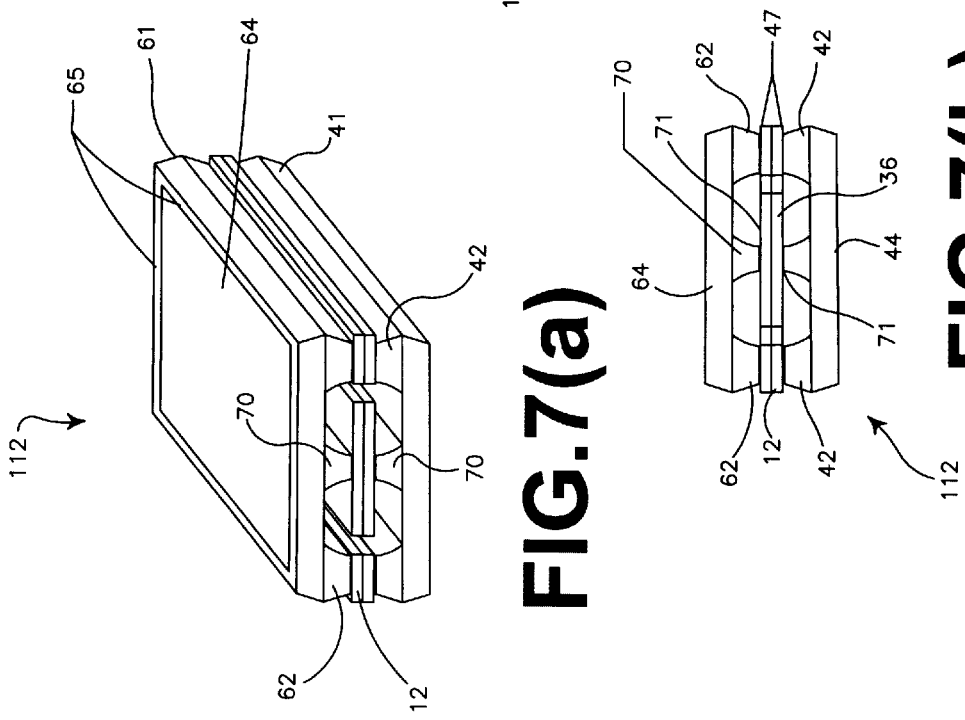
FIG. 7(c)
FIG. 7(a)
FIG. 7(b)

SHOCK RESISTANT ACCELEROMETER FOR IMPLANTABLE MEDICAL DEVICE

CROSS-REFERENCE TO RELATED APPLICATION

This patent application is a continuation-in-part of U.S. patent application Ser. No. 08/399,072 to Sikorski et al. filed Mar. 8, 1995 entitled "Package Integrated Accelerometer," now U.S. Pat. No. 5,674,258, the disclosure of which is hereby incorporated by reference herein in its entirety.

BACKGROUND OF THE INVENTION

The present invention relates generally to accelerometers, and finds particularly efficacious application in implantable cardiac pacemakers as an accelerometer for generating an electrical output signal indicative of a patient's activity.

Present day piezoceramic cantilevered beams are well understood in the area of cardiac pacing, as well as the equations which govern their characteristics. Conventional electrical and mechanical connection of the beam is typically accomplished by clamping onto the short edge of the beam to produce a cantilever configuration defining an overall beam length.

U.S. Pat. No. 4,140,132 to Dahl describes piezoceramic material in a physical activity sensor or accelerometer An elongated piezoelectric cantilevered element is disclosed as having a weighted mass on one end of the element, and as being enclosed within an implanted cardiac pacemaker.

U.S. Pat. No. 5,235,237 to Leonhardt discloses a piezoceramic bending beam accelerometer enclosed within a housing where surface mount technology is employed. One end of the packaged accelerometer is clamped down within an enclosed package.

U.S. Pat. No. 4,653,326 to Danel et al. describes an accelerometer capable of measuring a component of acceleration by means of a variable capacitance capacitor.

U.S. Pat. No. 5,031,615 to Alt discloses a pacemaker which employs an accelerometer comprising a miniaturized mechanoelectrical converter or transducer formed in a semiconductor device.

The inventions disclosed in preceding references have certain disadvantages. For example, the beam connection to the package or pacemaker shield becomes a dominant factor in determining the sensitivity of the accelerometer when employing a bonding medium of either solder or conductive epoxy. When bonding, the medium may bleed onto the beam and result in a reduced effective net length of the beam as well as attenuation of piezoceramic sensitivity. Hence, the bonding step can adversely affect the overall beam performance and contribute to manufacturing yield loss. Additionally, many bonding methods require complex and expensive packing techniques to ensure a robust design.

Some prior art pacemaker accelerometers suffer from excessive mechanical fragility to the extent that the center cantilever beams thereof break, fracture or otherwise fail when the pacemakers are dropped onto hard surfaces from heights of only a few feet or inches.

SUMMARY OF THE INVENTION

The present invention overcomes the disadvantages of the prior art by providing a method of and apparatus for coupling an accelerometer within a cardiac pacemaker, and by providing a structure which improves substantially the shock survivability of same.

The present invention has certain objects. That is, the present invention provides solutions to certain problems existing in the prior art such as implantable medical devices having accelerometers disposed therein that: (a) are excessively fragile or prone to fracturing, breakage or failure; (b) may break off, or have portions thereof that may break off, in response to a high acceleration event, the broken accelerometer or portion thereof potentially shorting out electrical or electronic circuitry disposed within the implantable medical device; (c) insufficiently reliable; and (d) prone to fracturing, breakage or other failure during manufacturing, final assembly, transportation or shipping, handling, implantation, or during ordinary operation while implanted in a human subject.

The accelerometer assembly of the present invention provides certain advantages, including: (a) decreased susceptibility to fracturing, breakage or other failure during manufacturing, final assembly, transportation or shipping, handling, implantation, or during ordinary operation while implanted in a human subject; (b) a low cost simple solution to the problems existing in the prior art; (c) surface mountability; (d) easy and simple cleaning of the internal cavity thereof, either before or after surface mounting to remove solidified droplets of solder, flux residue and the like; (e) increased reliability of implantable medical devices such as IPGs, pacemakers and PCDs containing the assembly; (f) the same or substantially the same voltage output as prior art devices, notwithstanding its various other advantages; and (g) reduced risk and increased safety for patients owing to increased reliability and reduced incidence of failure.

The accelerometer assembly of the present invention has certain features, including one or more stops disposed within the central cavity thereof, the stops being generally disposed above or below, or above and below, the upper and lower surfaces of a central beam in a piezoelectric accelerometer. The stops restrict or limit the extent to which the beam of the accelerometer may deflect or move along an imaginary vertical axis, and do not permit the beam to deflect a distance sufficiently large to enable fracturing, breakage or other physical damage or failure to be sustained thereby. The stops may form rails, protrusions, wedges, rectangles or other shapes integral to or separate from, but nevertheless attached to, the upper and lower housing members of the accelerometer assembly. Alternatively, the stops may comprise strips of foam tape applied to the upper and lower surfaces of the beam of the accelerometer, dabs of silicone or like material applied to the upper and lower surfaces of the beam or to the inwardly-facing surfaces of the upper and lower housing members. Finally, the stops may be formed by filling the central cavity with a suitably viscous damping gel or liquid, and containing such gel or liquid within the cavity by emplacing front and rear covers on the accelerometer assembly. Methods of making and using the foregoing assemblies and components also fall within the scope of the present invention.

Other features, advantages and objects of the present invention will become more apparent by referring to the appended drawings, detailed description and claims.

BRIEF DESCRIPTION OF THE DRAWINGS

FIG. 4 (FIGS. 4A–4E) shows a diagrammatic representation of the steps corresponding to one method of the present invention;

FIGS. 6(a) through 6(f) show selected views and preferred dimensions of one embodiment of accelerometer 12 and lower housing member 41 of the present invention;

FIGS. 7(a) through 7(c) show selected views of a preferred embodiment of the accelerometer assembly of the present invention;

DESCRIPTION OF THE PREFERRED EMBODIMENTS

Figure 1:
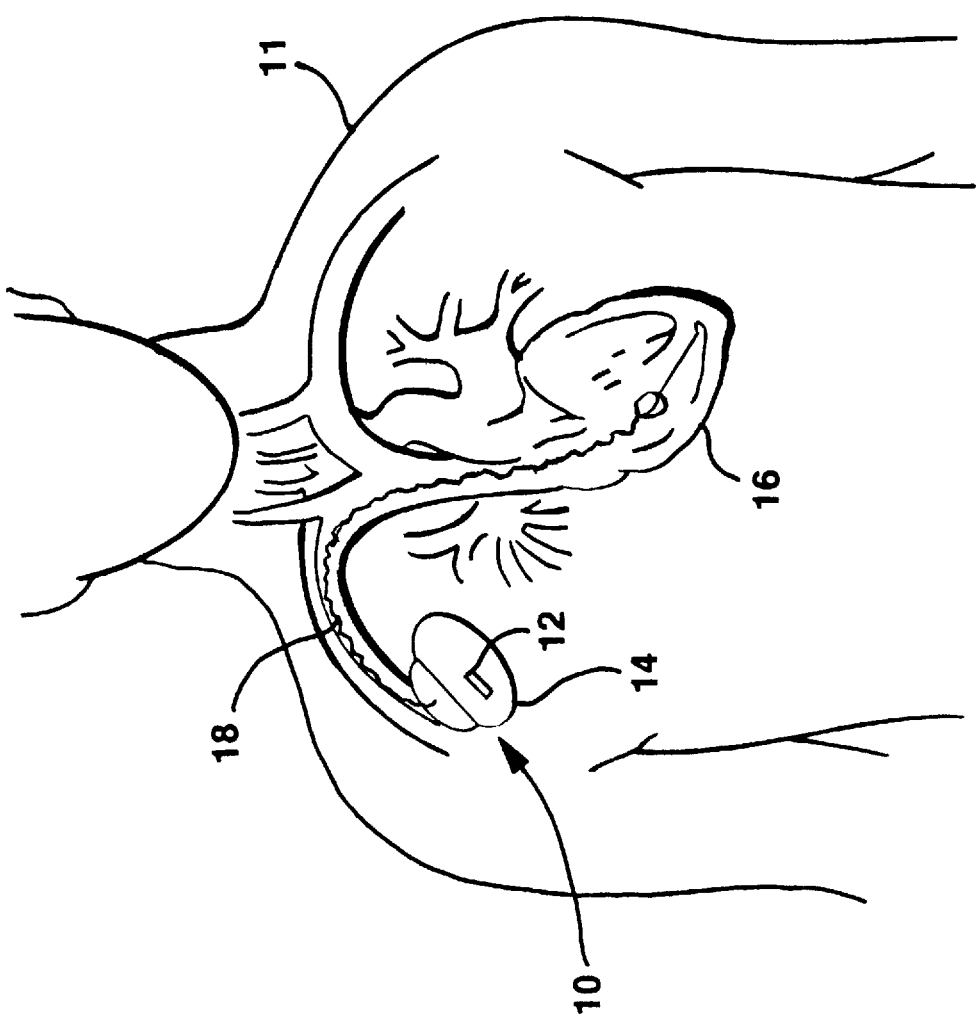
FIG. 1 shows an implantable medical device in accordance with one embodiment of the present invention.

FIG. 1 shows the placement of pacemaker 10 in accordance with one embodiment of the present invention in a human subject. Pacemaker 10 is shown in FIG. 1 as it would be implanted in a patient 11. The preferred embodiment of the invention includes an activity sensor 12, which is a piezoceramic accelerometer disposed on the hybrid circuit and isolated from the housing 14 of pacemaker 10. Pacemaker 10 may additionally include other sensors, such as a pressure sensor or the like implanted within heart 16 or disposed on the distal end of pacemaker lead 18.

A pacemaker which measures the physical activity of a patient by means of a piezoelectric transducer disposed on the housing of the pacemaker is disclosed in U.S. Pat. No. 4,485,813 to Anderson et al., hereby incorporated by reference herein in its entirety. U.S. Pat. No. 5,031,615 to Alt discloses another example of an activity-sensing cardiac pacemaker which includes an integrated miniaturized accelerometer.

It is to be understood that the present invention is not limited in scope to either single-sensor or dual-sensor pacemakers, and that other sensors besides activity and pressure sensors could be used in practicing the present invention. Nor is the present invention limited in scope to single-chamber pacemakers. The present invention may also be practiced in connection with multiple-chamber (e.g., dual-chamber) pacemakers.

Figure 2:
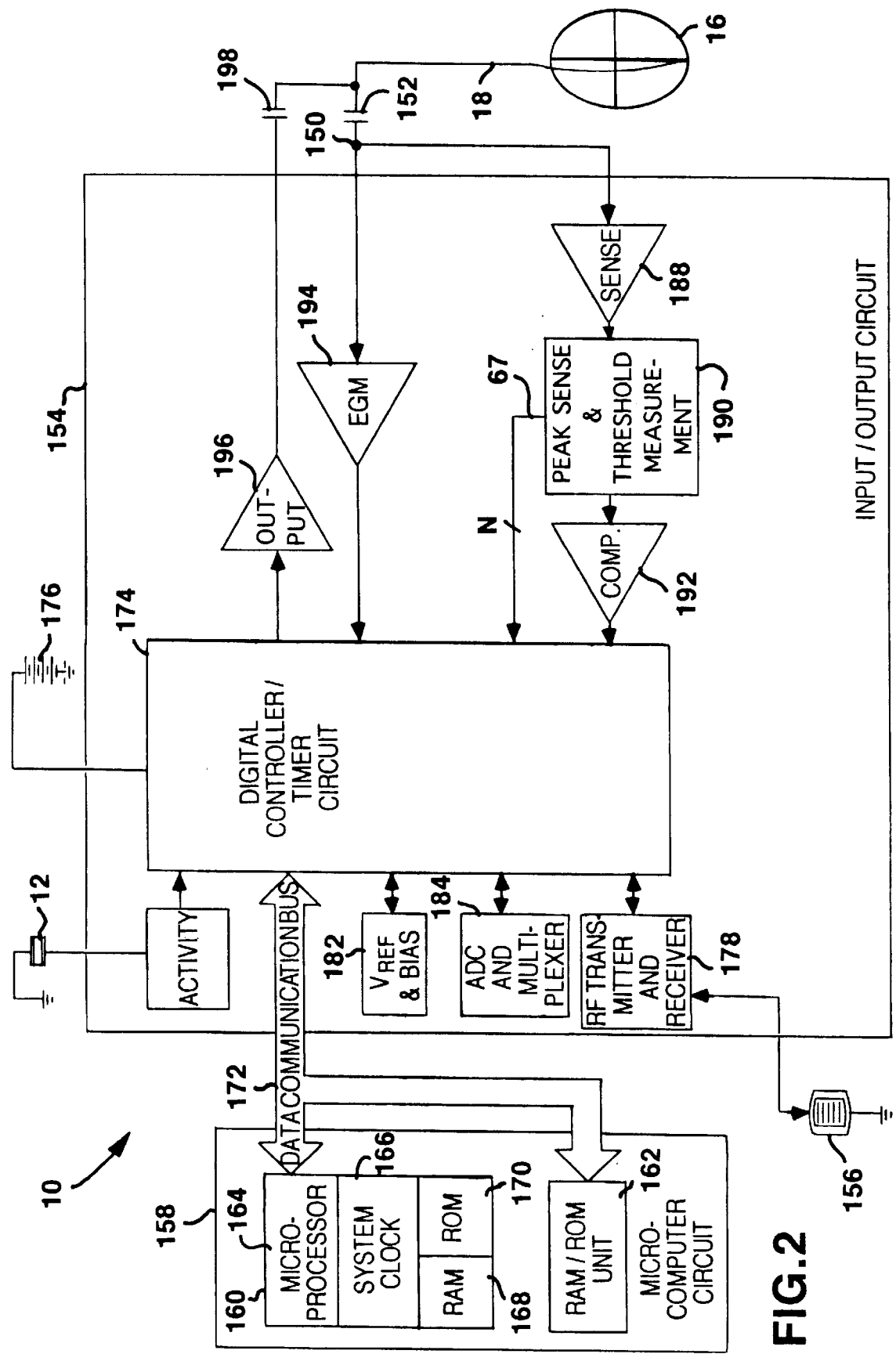
FIG. 2 shows a block diagram of a pacemaker in accordance with one disclosed embodiment of the present invention.

FIG. 2 shows a block diagram illustrating the constituent components of a pacemaker 10 in accordance with one embodiment of the present invention, where pacemaker 10 has a microprocessor-based architecture. The present invention may be utilized in conjunction with other implantable medical devices, however, such as cardioverters, defibrillators, cardiac assist systems, and the like, or in conjunction with other design architectures.

In the illustrative embodiment shown in FIG. 2, pacemaker 10 includes an activity sensor 12, which is preferably a piezoceramic accelerometer bonded to the hybrid circuit inside the pacemaker housing. Piezoceramic accelerometer sensor 12 provides a sensor output which varies as a function of a measured parameter that relates to the metabolic requirements of patient.

Pacemaker 10 of FIG. 2 is most preferably programmable by means of an external programming unit (not shown in the Figures). One such programmer suitable for the purposes of the present invention is the commercially available Medtronic Model 9790 programmer. The programmer is a microprocessor device which provides a series of encoded signals to pacemaker 10 by means of a programming head which transmits radio-frequency (RF) encoded signals to pacemaker 10 according to a telemetry system such as that described in U.S. Pat. No. 5,312,453 to Wyborny et al., the disclosure of which is hereby incorporated by reference herein in its entirety. It is to be understood, however, that the programming methodology disclosed in Wyborny et al. patent is identified herein for the illustrative purposes only, and that any programming methodology may be employed so long as the desired information is transmitted to and from the pacemaker. One of skill in the art may choose from any of a number of available programming techniques to accomplish this task.

Pacemaker 10 is schematically shown in FIG. 2 to be electrically coupled to a pacing lead 18 disposed in patient's heart 16. Lead 18 preferably includes an intracardiac electrode disposed at or near its distal end and positioned within the right ventricular (RV) or right atrial (RA) chamber of heart 16. Lead 18 may have unipolar or bipolar electrodes disposed thereon, as is well known in the art. Although an application of the present invention in the context of a single-chamber pacemaker is disclosed herein for illustrative purposes, it is to be understood that the present invention may equally well be applied in the context of a dual-chamber pacemakers or other implantable device.

Lead 18 is coupled to a node 150 in the circuitry of pacemaker 10 through input capacitor 152. In the presently disclosed embodiment, accelerometer 12 is attached to the hybrid circuit inside pacemaker 10, and is not shown explicitly in FIG. 2. The output from accelerometer 12 is coupled to input/output circuit 154. Input/output circuit 154 contains analog circuits for interfacing to heart 16, accelerometer 12, antenna 156, and circuits for the application of stimulating pulses to heart 16 to control its rate under control of software-implemented algorithms in microcomputer circuit 158.

Microcomputer circuit 158 preferably comprises on-board circuit 160 and off-board circuit 162. Circuit 158 may correspond to the microcomputer circuit disclosed in U.S. Pat. No. 5,312,453 to Shelton et al., the disclosure of which is hereby incorporated by reference herein in its entirety. On-board circuit 160 includes microprocessor 164, system clock circuit 166, and on-board RAM 168 and ROM 170. In the presently disclosed embodiment of the invention, off-board circuit 162 comprises a RAM/ROM unit. On-board circuit 160 and off-board circuit 162 are each coupled by a data communication bus 172 to a digital controller/timer circuit 174. Microcomputer circuit 158 may form a custom integrated circuit device augmented by standard RAM/ROM components. The electrical components shown in FIG. 2 are powered by an appropriate implantable battery power source 176, in accordance with common practice in the art. For the sake of clarity, the coupling of battery power to the various components of pacemaker 10 is not shown in the Figures.

Antenna 156 is connected to input/output circuit 154 to permit uplink/downlink telemetry through RF transmitter and receiver unit 178. Unit 178 may correspond to the telemetry and program logic disclosed in U.S. Pat. No. 4,566,063 issued to Thompson et al., hereby incorporated by reference herein in its entirety, or to that disclosed in the above-referenced Wyborny et al. patent. The particular programming and telemetry scheme chosen is not believed to be critical for purposes of practicing the present invention so long as entry and storage of values of rate-response parameters are permitted.

$V_{REF}$ and Bias circuit 182 generates a stable voltage reference and bias currents for the analog circuits of input/output circuit 154. Analog-to-digital converter (ADC) and multiplexer unit 184 digitizes analog signals and voltages to provide "real-time" telemetry intracardiac signals and battery end-of-life (EOL) replacement function.

Operating commands for controlling the timing of pacemaker 10 are coupled by data bus 172 to digital controller/timer circuit 174, where digital timers and counters establish the overall escape interval of the pacemaker as well as various refractory, blanking and other timing windows for controlling the operation of the peripheral components disposed within input/output circuit 154.

Digital controller/timer circuit 174 is preferably coupled to sensing circuitry, including sense amplifier 188, peak sense and threshold measurement unit 190 and comparator/threshold detector 192. Circuit 174 is further preferably coupled to electrogram (EGM) amplifier 194 for receiving amplified and processed signals sensed by an electrode disposed on lead 18. Sense amplifier 188 amplifies sensed electrical cardiac signals and provides an amplified signal to peak sense and threshold measurement circuitry 190, which in turn provides an indication of peak sensed voltages and measured sense amplifier threshold voltages on multiple conductor signal path 67 to digital controller/timer circuit 174. An amplified sense amplifier signal is then provided to comparator/threshold detector 192. Sense amplifier 188 may correspond to that disclosed in U.S. Pat. No. 4,379,459 to Stein, which is hereby incorporated by reference herein in its entirety.

The electrogram signal provided by EGM amplifier 194 is employed when the implanted device is being interrogated by an external programmer (not shown) to transmit by uplink telemetric means a representation of an analog electrogram of the patient's electrical heart activity. See, for example, U.S. Pat. No. 4,556,063 to Thompson et al., hereby incorporated by reference herein in its entirety. Output pulse generator 196 provides pacing stimuli to patient's heart 16 through coupling capacitor 198 in response to a pacing trigger signal provided by digital controller/timer circuit 174 each time the escape interval times out, an externally transmitted pacing command is received, or in response to other stored commands as is well known in the pacing art. Output amplifier 196 may correspond generally to the output amplifier disclosed in U.S. Pat. No. 4,476,868 to Thompson, also incorporated by reference herein in its entirety.

While specific embodiments of input amplifier 188, output amplifier 196 and EGM amplifier 194 have been identified herein, this is done for the purposes of illustration only.

The specific embodiments of such circuits are not critical to practicing the present invention so long as the circuits provide means for generating a stimulating pulse and are capable of providing digital controller/timer circuit 174 with signals indicative of natural or stimulated contractions of the heart.

Figure 3:
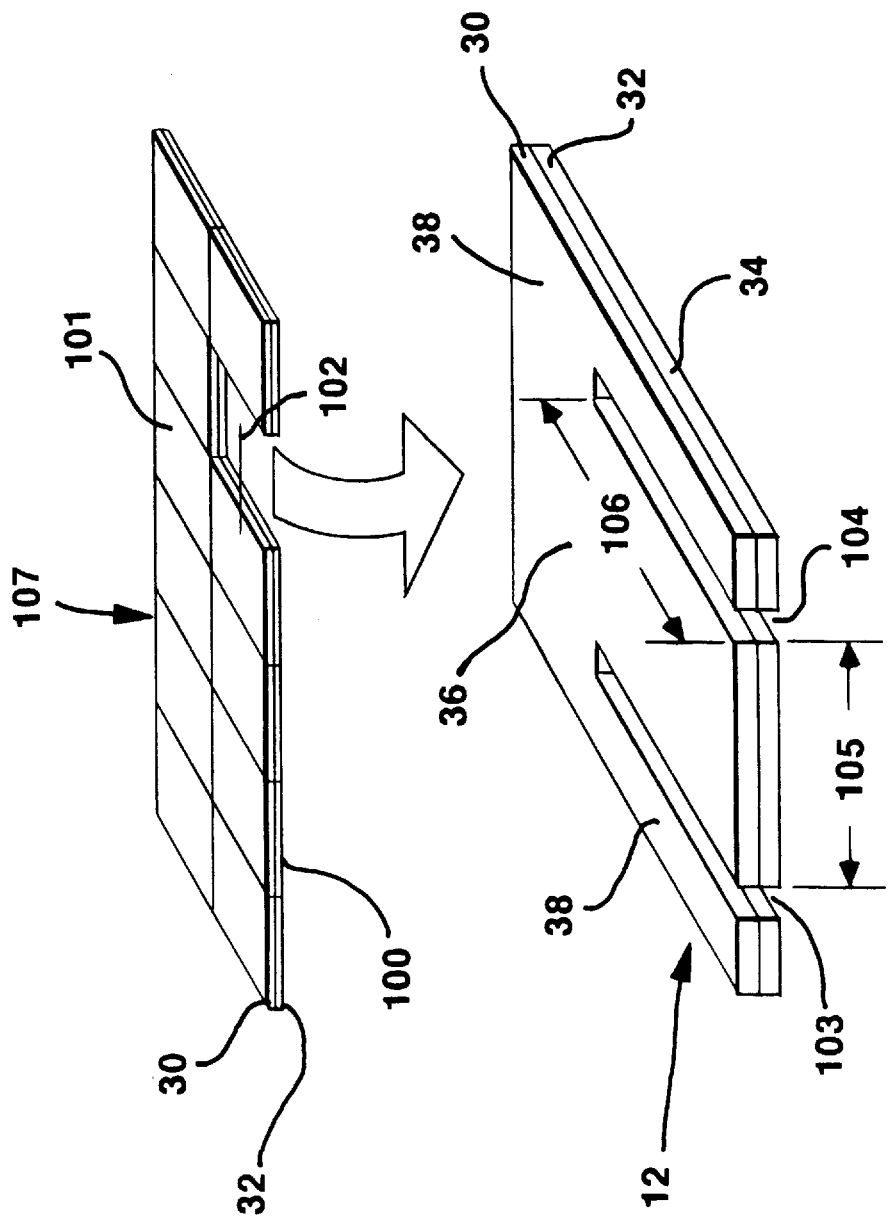
FIG. 3 shows a perspective view of an accelerometer in accordance with one disclosed embodiment of the present invention.

FIG. 3 schematically illustrates portions of one method of manufacturing a component accelerometer 12 of the present invention. Upper and lower sheets 30 and 32 comprise a piezoelectric material such as lead zirconate titanate, quartz, lithium niobate, lithium titanate or any other suitable material having the desired piezoelectric properties. Sheets 30 and 32 may each be formed from multiple layers of tape, or may alternatively each form a single monolithic layer formed from, for example, freeze-dried granules of suitable piezoelectric material that are subsequently compressed together. Sheets 30 and 32 are bonded together to form a multi-layer structure, and are most preferably separated by interposing platinum metallization layer or plating 39. This multi-layer structure is then usually co-fired, followed by subsequent deposition or plating of nickel electrode layers 100 and 101 on the upper and lower surfaces of sheet 107.

Next, upper and lower sheets 30 and 32 of piezoelectric sheet 107 are electrically polarized in appropriate orientations by known conventional means to yield a sheet having the desired piezoelectric properties. That is, the respective orientations of the principal electrical axes corresponding to upper and lower sheets 30 and 32 are defined during a polarizing step. Sheet 107 is then cut into smaller rectangular elements with a ceramic cutting saw.

Next, the step of defining active area 36 (the cantilever beam) and inactive area 35 (which is employed couple accelerometer 12 to a hybrid circuit) is performed by using a diamond bladed wheel to cut notches 103 and 104. Incisions or notches 103 and 104 separate inactive and active areas of accelerometer 12. The incisions into the piezoelectric material also define the sensitivity of the accelerometer by controlling resulting beam width 105 and length 106.

Preferred dimensions for accelerometer 12 are about 0.133 inches for length 106 of notches 103 and 104; about 0.010 inches for the width 113 of notch 103 or 104; about 0.080 inches for width 105 of beam 36; about 0.025 inches for width 109 of arms 49; about 0.014 inches for overall thickness 102 of accelerometer 12; and about 0.047 inches for length 108 of inactive area 35. In preferred embodiments of the present invention, substantially vertical deflection of beam 35 along imaginary axis V is limited to distances not exceeding about 0.002 inches through the action of stop 70 shown in FIGS. 4A through 4E and 6(a) through 15(c). Additionally, and also in preferred embodiments of the present invention, substantially vertical deflection of beam 35 along imaginary axis V is limited to distances not exceeding about 0.0005 inches through the action of stop 70. FIGS. 6(a) through 6(e) show further preferred dimensions for most of the components comprising accelerometer assembly 112. Of course, dimensions and beam deflection ranges other than those set forth explicitly herein are also contemplated in the present invention.

ENDEVCO™ of San Juan Capistrano, Calif. and MORGAN COMPANY™ of Bedford, Ohio supply suitable materials for forming accelerometers 12 of the present invention. Both companies are also capable of providing fully machined and formed accelerometers 12.

FIG. 4 shows some of the steps required to form accelerometer assembly 112 from lower component 41, accelerometer 12, upper component 61, conductive thermoplastic or epoxy 47 and stop 70. FIG. 4A shows lower housing member 41. Upper housing member 61, not shown in FIG. 4A, most preferably assumes the same shape and structure as lower housing member 41, but is oriented to face lower housing member 41 such that downwardly extending arms 62 of upper housing member 61 align with upwardly extending arms 42 of lower housing member 41. Stops 70 of upper and lower housing members 61 and 41 limit the vertical range of motion of beam 35 when beam 35 deflects in response to being subjected to a suitably great force or acceleration. By limiting the vertical range of motion through which beam 35 may move, stops 70 prevent beam 35 from failing or fracturing as a result of excessive deflection. Stops 70 may be incorporated into upper housing member 61 alone, lower housing member 41 alone, or most preferably into both upper and lower housing members 61 and 41.

Upper and lower housing members 41 and 61 are most preferably formed from blocks of Kovar or Alloy 42, where the blocks are chemically etched to provide the desired structural shape and outlines of those members, followed by nickel-gold alloy plating of the exterior surfaces thereof to reduce or eliminate oxidation. Kovar and Alloy 42 have been found to provide the advantages of being structurally robust, inexpensive, chemically etchable and platable with alloys or metals for preventing oxidation. NORTHWEST ETCH TECHNOLOGY™ of Tacoma, Wash. provides Kovar etching services suitable for practicing the present invention. JOHNSON MATTHEY, INC.™ of Washington State provides nickel-gold alloy plating services suitable for practicing the present invention.

Other materials such as copper, aluminum, brass, nickel, platinum and other noble metals, and conductive carbon composites, suitable ceramic compositions or plastic capable of accepting metallic plating on the exterior surfaces thereof, may be employed to form upper and lower housing members 41 and 61. Upper and lower housing members 41 and 61 may also be machined, milled or stamped from blocks of suitable material.

Outer members 49 of accelerometer 12 are employed to mount accelerometer 12 within a low cost protective package in accordance with a preferred embodiment of the present invention. In FIG. 4A, lower housing member 41 preferably assumes "W" shaped cross-section 43 to permit suitable vertical movement of beam 36. Lower housing member 41 and upper housing member 61 are most preferably formed to contact only outer arms or members 49.

Electrically conductive material 47 is disposed on at least portions of the upper surfaces of upwardly extending arms 42 and the lower surfaces of downwardly extending arms 62 before accelerometer 12 is mounted and sandwiched therebetween.

Electrically conductive material 47 may comprise any of a number of materials such as a suitable electrically conductive epoxy or other glue. Electrically conductive material 47 most preferably comprises a thermoplastic such as STAY-STIK™ 181 silver-filled paste manufactured by ALPHA METALS198 of Jersey City, N.J. In a preferred embodiment of the present invention, material 47 is a STAYSTIK wet paste formulation containing a resin and a diluent that is applied, respectively, onto the top and bottom surfaces of upwardly extending arms 42 and downwardly extending arms 62 by a conventional screening process employing a metal stencil. Such a wet paste formulation is preferably laid down on those top and bottom surfaces in layers about 0.005 inches thick. Upper and lower housing members 61 and 41 containing the so-applied paste are then dried in an oven containing a nitrogen atmosphere at temperatures ranging between about 200 degrees F and about 300 degrees F for periods of time ranging between about 45 minutes and about 90 minutes.

As shown in FIG. 4D, and following drying of the thermoplastic, lower housing member 41 is placed in tool 66, accelerometer 12 is placed atop lower housing member 41, and upper housing member 61 is placed atop accelerometer 12 such that outward arms 49 of accelerometer 12 are sandwiched or interposed between upwardly extending arms 42 of lower housing member 41 and downwardly extending arms 62 of upper housing member 61. Material 47 forms an electrical connection and mechanical bond between the upper metal plated surfaces of upwardly extending arms 42 of lower housing member 41, the lower metal-plated surfaces of downwardly extending arms 62 of upper housing member 61, and upper and lower housing members 61 and 41. A compression spring applying between about 8 and about 24 ounces of force is then positioned atop assembly 112, and assembly 112 and the spring are placed in an oven containing a nitrogen atmosphere having a temperature of about 400 degrees F for about 60 minutes. Assembly 112 is then removed from the oven and permitted to cool.

Assembly process 40 of FIG. 4 terminates upon the completion of the final step shown in FIG. 4E. Accelerometer assembly 112 is preferably tested and characterized prior to coupling first terminal 44 of assembly 112 with lead/tin solder 53 to a hybrid (not shown in FIG. 4E) and coupling by ultrasonic wire bonding means second terminal 64 to the hybrid by aluminum or gold wire bond 55.

The protective packaging process of the present invention enhances manufacturing yields by reducing or eliminating variability in the amplitude of the output signal to thereby provide a consistent, reliable means for attaching accelerometer 12 to the protective package defined by assembly 112. Moreover, the output signal provided by assembly 112 may be increased by twisting and mechanically biasing sensor base 35 of accelerometer 12 during the accelerometer assembly forming process. The manner in which outer members 49 of accelerometer 12 are bonded to upper and lower housing members 61 and 41 may also add to or diminish the amplitude of the output signal provided by assembly 112. For example, if electrically conductive thermoplastic or epoxy is applied from a point near or on base 35 of accelerometer 12 to a point near the opposite end of accelerometer 12 along outer members 49, twisting of accelerometer 12 in the region defined by base 35 is diminished, and hence the overall output signal provided by accelerometer 12 is reduced in amplitude. As the amount of material 47 applied to the region near base 35 decreases, twisting of accelerometer 12 in the region defined by base 35 increases, thereby increasing the amplitude of the output signal provided by accelerometer 12.

Figure 5A:
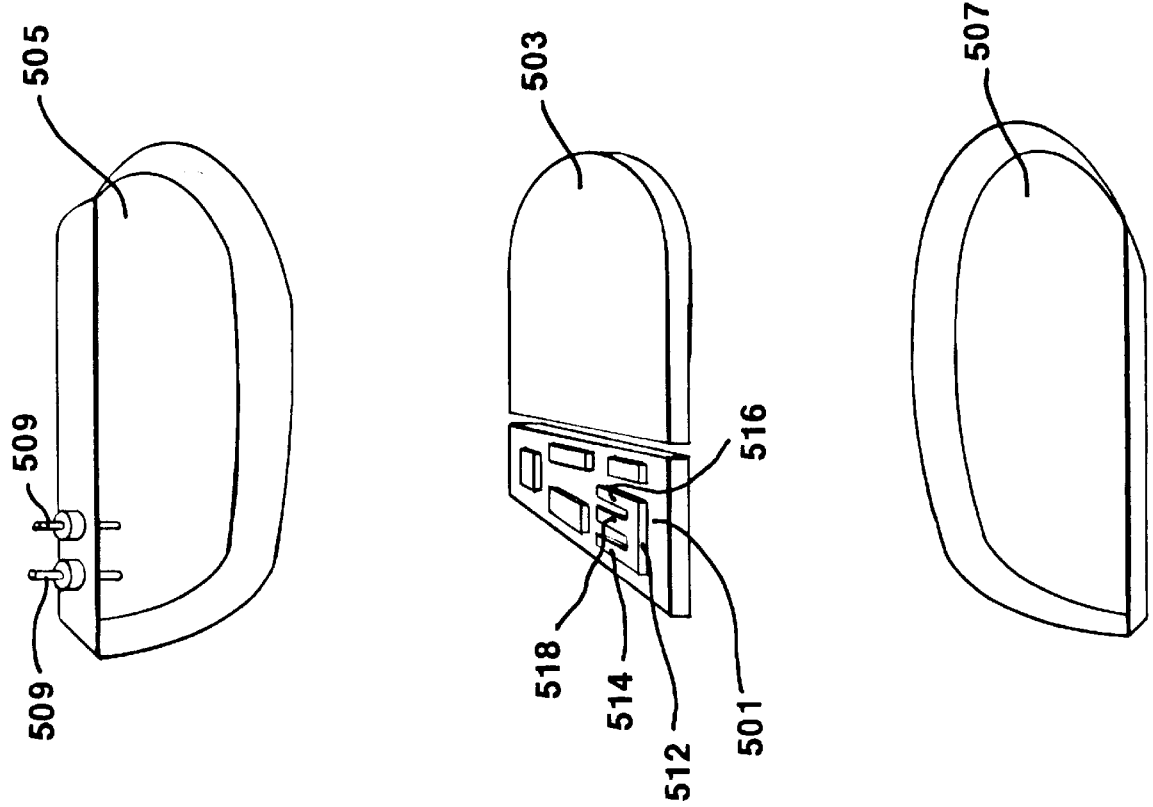
FIG. 5 shows an exploded perspective view of an implantable medical device of the present invention and corresponding electronics hermetically sealed therein.
Figure 5B:
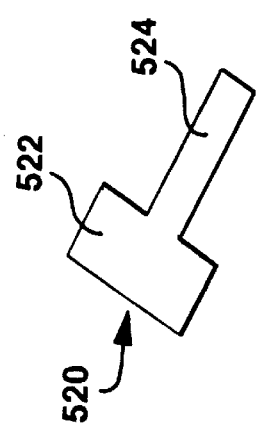

FIG. 5 illustrates one manner in which an assembled medical device such as a cardiac pacemaker may be formed by mounting one or more feedthroughs 509 to shields 505 and 507. Internal electronics such as pulse generator circuitry, accelerometer assembly 112 and battery or electrochemical cell 503 are disposed within shields 505 and 507. Battery 503 is coupled to circuitry through additional feedthroughs that are not shown in the Figures. Shields 505 and 507 are preferably laser welded together along their edges to form an hermetic enclosure. A molded plastic connector block assembly (not shown in the Figures) containing electrical connectors for attachment of medical leads to feedthroughs 509 is typically installed atop shields 505 and 507 sometime thereafter.

In FIG. 5, accelerometer assembly permits direct attachment thereof to a hybrid circuit. Accelerometer assembly 112 is preferably attached to such a circuit by solder reflow or conductive epoxy film or adhesive means. Such means provide an electrical connection to bottom electrode 44 of accelerometer assembly 112 and elevate accelerometer assembly 112 from the hybrid substrate surface. Furthermore, the attachment process described above substantially reduces or eliminates the variability of the electrical output signal provided by accelerometer 12 through the provision of a consistent, reliable means for attaching accelerometer 12 to the pacemaker hybrid. The amplitude of the electrical output signal of accelerometer 12 may also be adjusted by reducing the amount of metallization disposed on the top or bottom portions of beam 36 using conventional laser trimming means to reduce the effective net length thereof.

FIGS. 7(a) through 7(c) show selected views of a preferred embodiment of the accelerometer assembly of the present invention. More particularly, FIG. 7(a) shows a perspective view of a preferred embodiment of accelerometer assembly 112 of the present invention. FIG. 7(c) shows an exploded perspective view of assembly 112 of FIG. 7(a) and FIG. 7(b) shows a front end view of assembly 112 of FIG. 7(a). In FIGS. 7(a) through 7(c), stop 70 forms a central rail extending along the central length of lower and upper housing members 41 and 61. Upper and lower housing members 61 and 41 are shown in FIGS. 7(a) and 7(c) as being bonded together by electrically conductive material 47 (most preferably formed of thermoplastic) at the points where upwardly extending arms 42 and downwardly extending arms 62 meet the top and bottom surfaces of accelerometer 12. Second terminal 64 most preferably provides a wire-bondable surface for establishing electrical connection thereto. Edge area 65 most preferably defines a non-bondable strip or perimeter about 0.006 inches wide that surrounds second terminal 64. First terminal 44 most preferably provides a wire bondable or solderable surface for establishing electrical connection thereto. Gap 71 is disposed between stops 70 and the adjoining upper and lower surfaces of beam 36, and in preferred embodiments of the present invention does not exceed about 0.002 inches in height, and most preferably is about 0.0005 inches in height.

Figure 8A:
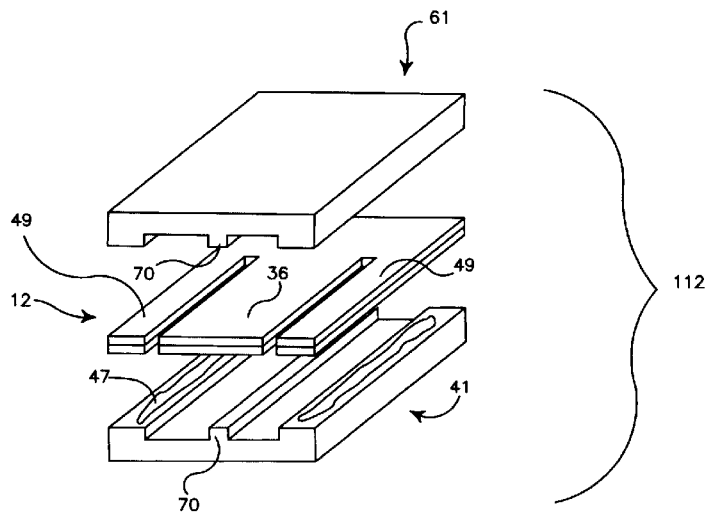
FIGS. 8(a) through 8(c) show a second embodiment of the of the accelerometer assembly of the present invention.
Figure 8B:
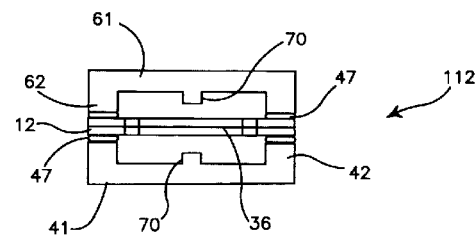
Figure 8C:
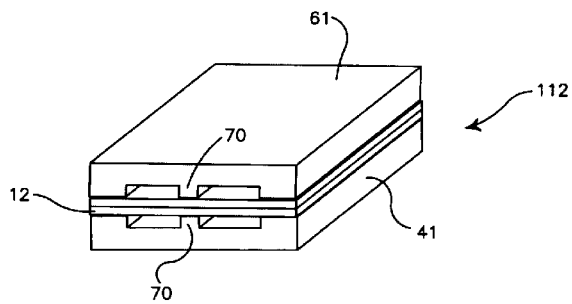

FIGS. 8(a) through 8(c) show a second embodiment of accelerometer assembly 112 of the present invention. FIG. 8(a) shows an exploded front top perspective view of the second embodiment. FIG. 8(c) shows a front top perspective view of the second embodiment. FIG. 8(b) shows a front end view of the second embodiment shown in FIG. 8(c). In FIGS. 8(a) through 8(c), stops 70 form rails positioned centrally along the lengths of upper and lower housing members 61 and 41.

Figure 9A:
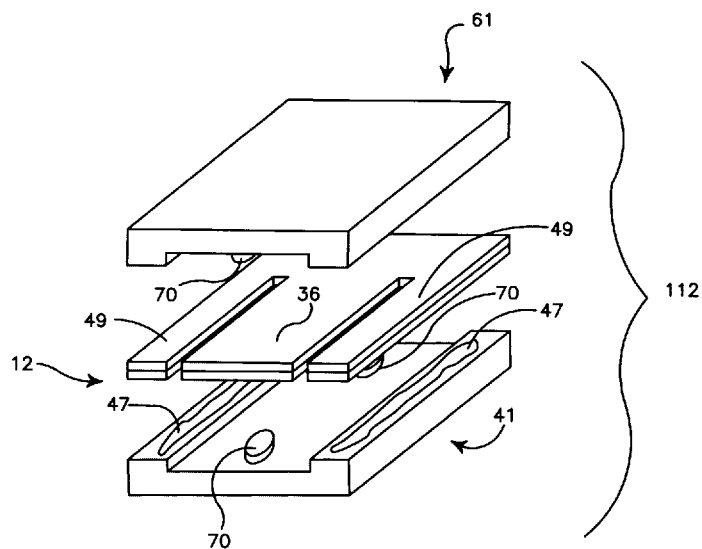
FIGS. 9(a) through 9(c) show a third embodiment of the of the accelerometer assembly of the present invention.
Figure 9B:
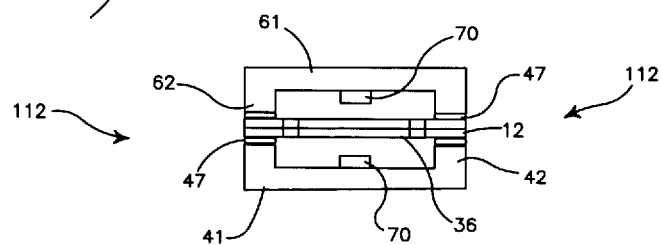
Figure 9C:
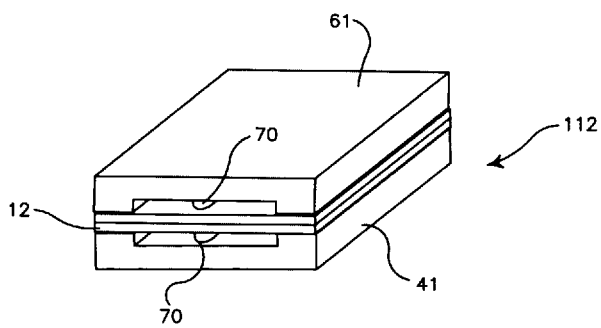

FIGS. 9(a) through 9(c) show a third embodiment of accelerometer assembly 112 of the present invention. FIG. 9(a) shows an exploded front top perspective view of the third embodiment. FIG. 9(c) shows a front top perspective view of the third embodiment. FIG. 9(b) shows a front end view of the third embodiment shown in FIG. 9(c). In FIGS. 9(a) through 9(c), stops 70 form posts or protrusions disposed near or at least the front ends of upper and lower housing members 61 and 41.

Figure 10A:
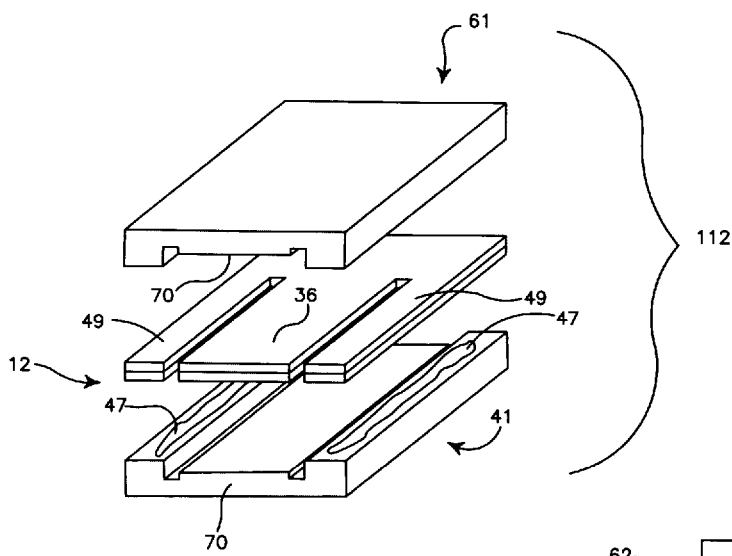
FIGS. 10(a) through 10(c) show a fourth embodiment of the of the accelerometer assembly of the present invention.
Figure 10B:
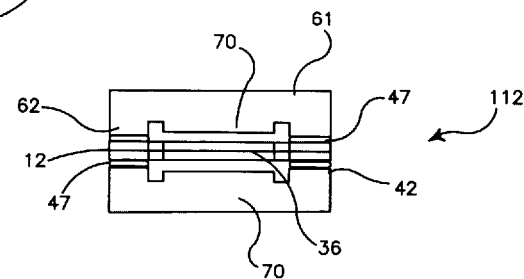
Figure 10C:
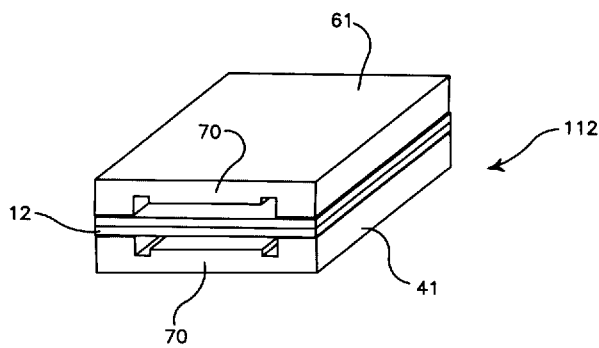

FIGS. 10(a) through 10(c) show a fourth embodiment of accelerometer assembly 112 of the present invention. FIG. 10(a) shows an exploded front top perspective view of the fourth embodiment. FIG. 10(c) shows a front top perspective view of the fourth embodiment. FIG. 10(b) shows a front end view of the fourth embodiment shown in FIG. 10(c). In FIGS. 10(a) through 10(c), stops 70 form wide rails positioned centrally along the lengths of upper and lower housing members 61 and 41.

Figure 11A:
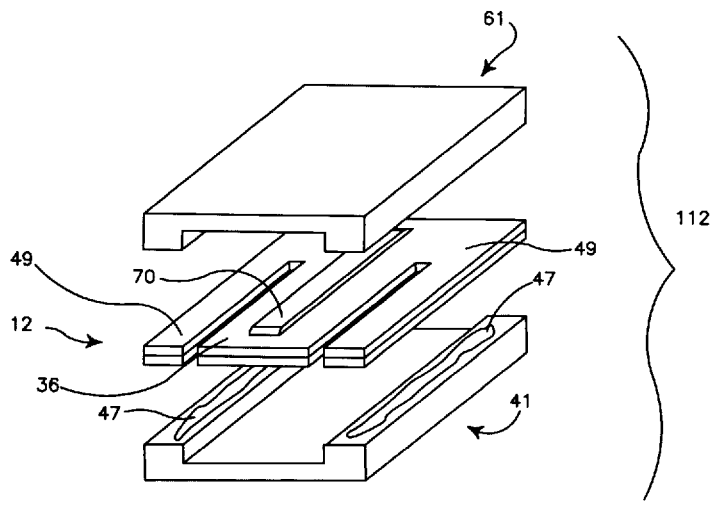
FIGS. 11(a) through 11(c) show a fifth embodiment of the of the accelerometer assembly of the present invention.
Figure 11B:
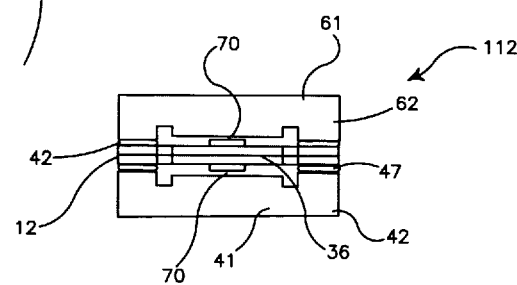
Figure 11C:
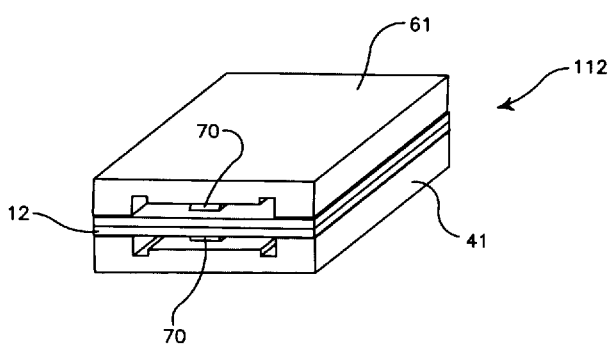

FIGS. 11(a) through 11(c) show a fifth embodiment of accelerometer assembly 112 of the present invention. FIG. 11(a) shows an exploded front top perspective view of the fifth embodiment. FIG. 11(c) shows a front top perspective view of the fifth embodiment. FIG. 11(b) shows a front end view of the fifth embodiment shown in FIG. 11(c). In FIGS. 11(a) through 11(c), stops 70 are formed from foam tape strips attached to the upper and lower surfaces of beam 36.

Figure 12A:
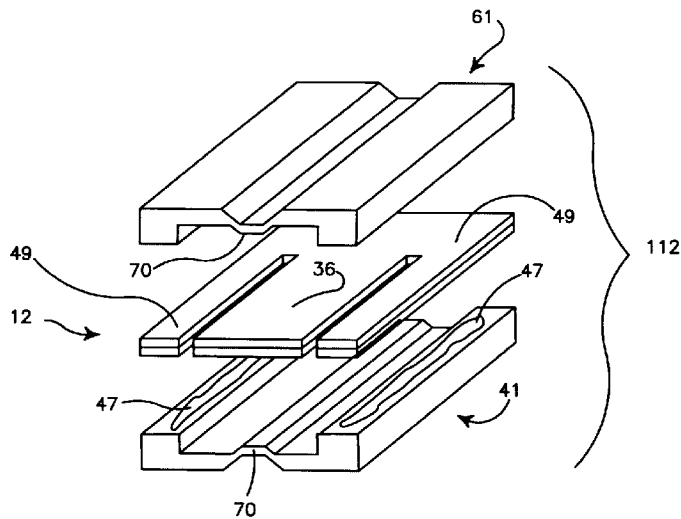
FIGS. 12(a) through 12(c) show a sixth embodiment of the of the accelerometer assembly of the present invention.
Figure 12B:
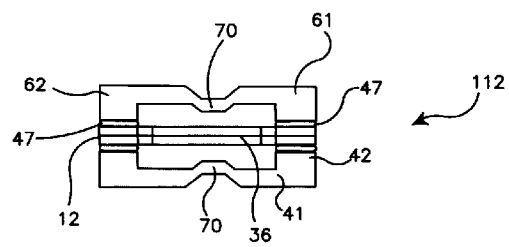
Figure 12C:
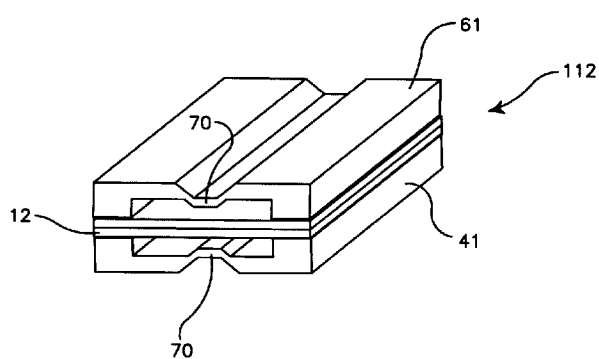

FIGS. 12(a) through 12(c) show a sixth embodiment of accelerometer assembly 112 of the present invention. FIG. 12(a) shows an exploded front top perspective view of the sixth embodiment. FIG. 12(c) shows a front top perspective view of the sixth embodiment. FIG. 12(b) shows a front end view of the sixth embodiment shown in FIG. 12(c). In FIGS. 12(a) through 12(c), stops 70 form upwardly and downwardly positioned rails located centrally along the lengths of upper and lower housing members 61 and 41.

Figure 13A:
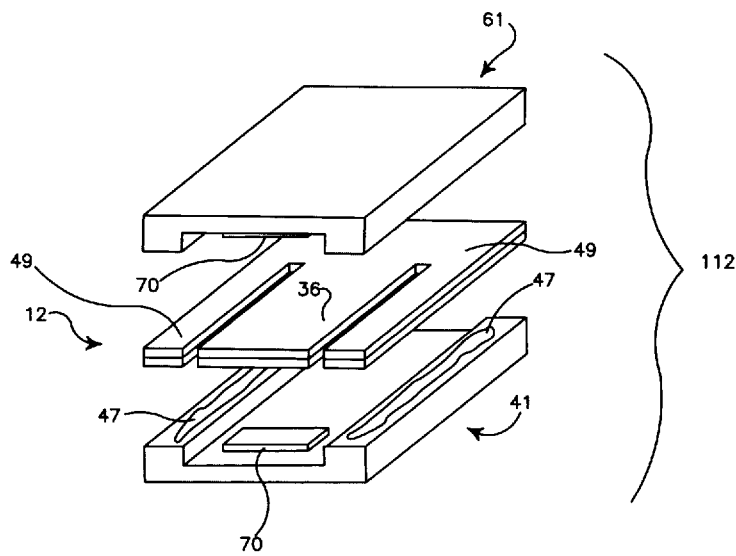
FIGS. 13(a) through 13(c) show a seventh embodiment of the of the accelerometer assembly of the present invention.
Figure 13B:
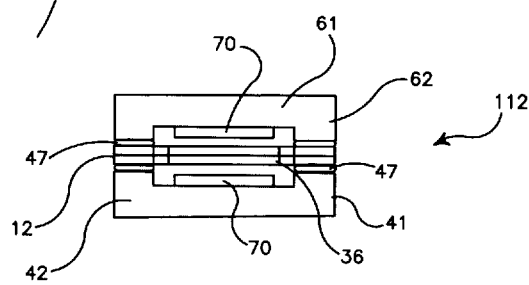
Figure 13C:
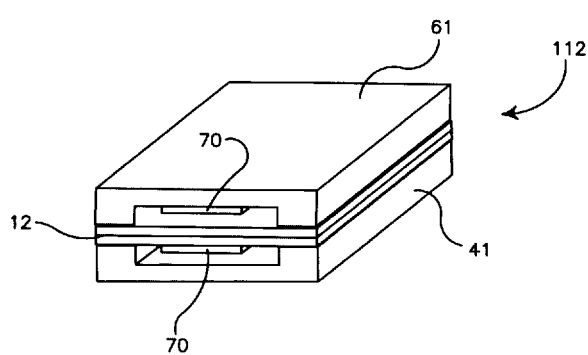

FIGS. 13(a) through 13(c) show a seventh embodiment of accelerometer assembly 112 of the present invention. FIG. 13(a) shows an exploded front top perspective view of the seventh embodiment. FIG. 13(c) shows a front top perspective view of the seventh embodiment. FIG. 13(b) shows a front end view of the seventh embodiment shown in FIG. 13(c). In FIGS. 13(a) through 13(c), stops 70 form rails positioned near the front portions of upper and lower housing members 61 and 41, the rails having a major axis positioned perpendicular to the lengths of upper and lower housing members 61 and 41.

Figure 14A:
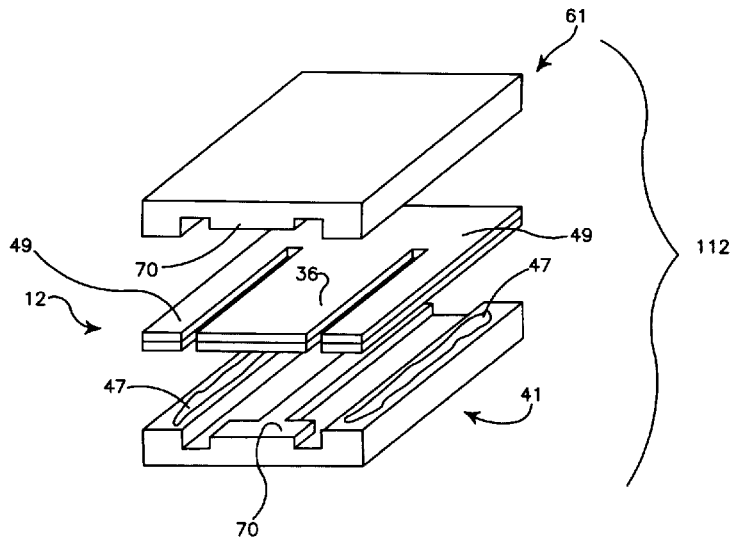
FIGS. 14(a) through 14(c) show a eighth embodiment of the of the accelerometer assembly of the present invention.
Figure 14B:
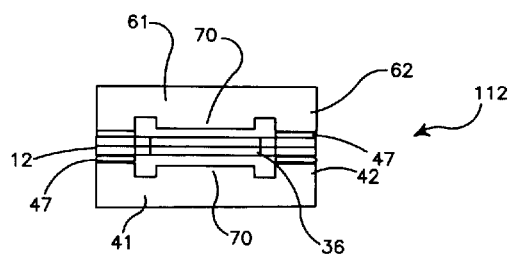
Figure 14C:
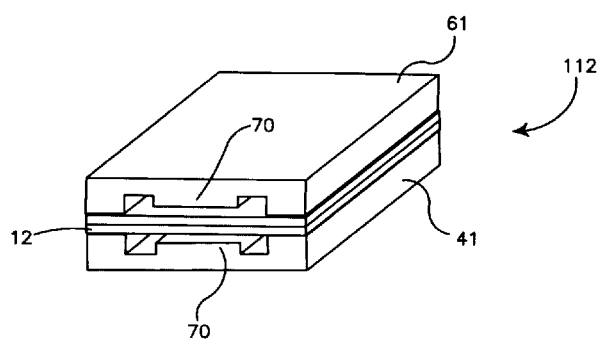

FIGS. 14(a) through 14(c) show an eighth embodiment of accelerometer assembly 112 of the present invention. FIG. 14(a) shows an exploded front top perspective view of the eighth embodiment. FIG. 14(c) shows a front top perspective view of the eighth embodiment. FIG. 14(b) shows a front end view of the eighth embodiment shown in FIG. 14(c). In FIGS. 14(a) through 14(c), stops 70 form T-shaped rails having major axes positioned centrally along the lengths of upper and lower housing members 61 and 41.

Figure 15A:
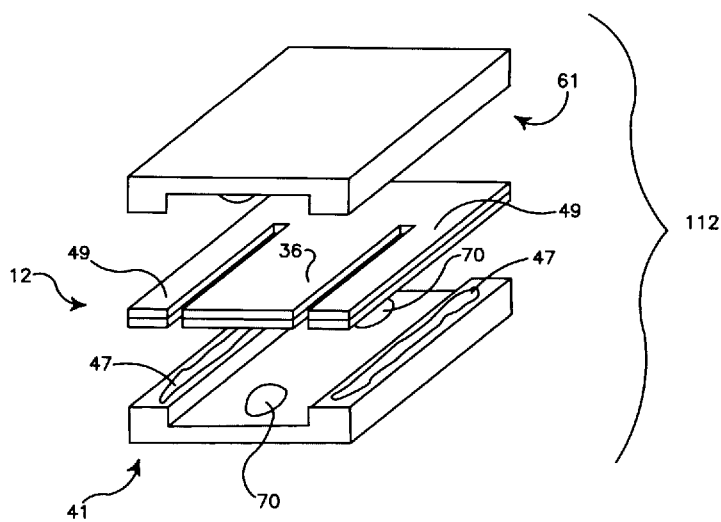
FIGS. 15(a) through 15(c) show a ninth embodiment of the of the accelerometer assembly of the present invention.
Figure 15B:
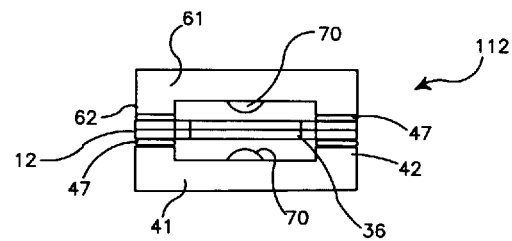
Figure 15C:
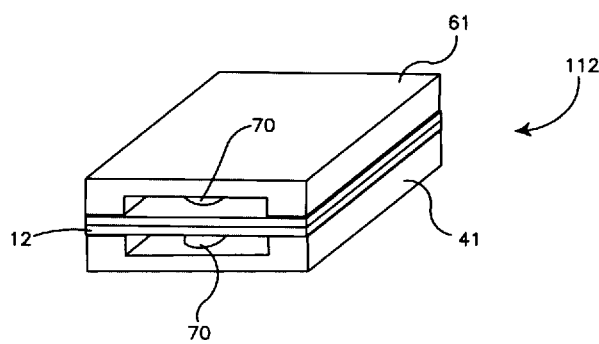

FIGS. 15(a) through 15(c) show a ninth embodiment of accelerometer assembly 112 of the present invention. FIG. 15(a) shows an exploded front top perspective view of the ninth embodiment. FIG. 15(c) shows a front top perspective view of the ninth embodiment. FIG. 15(b) shows a front end view of the ninth embodiment shown in FIG. 15(c). In FIGS. 15(a) through 15(c), stops 70 are formed of blobs or dabs of silicon or like elastic material that are emplaced initially in a semi-liquid, semi-fluid or otherwise flowable state on the inwardly-facing top and bottom central surfaces of upper and lower housing members 61 and 41, and thereafter permitted to dry.

Figure 16A:
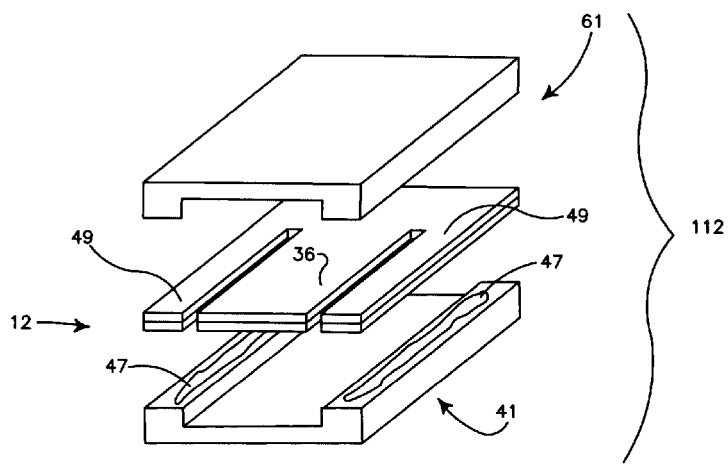
FIGS. 16(a) through 16(c) show a tenth embodiment of the of the accelerometer assembly of the present invention.
Figure 16B:
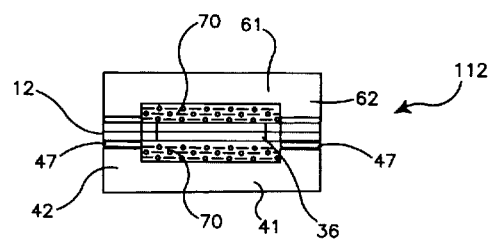
Figure 16C:
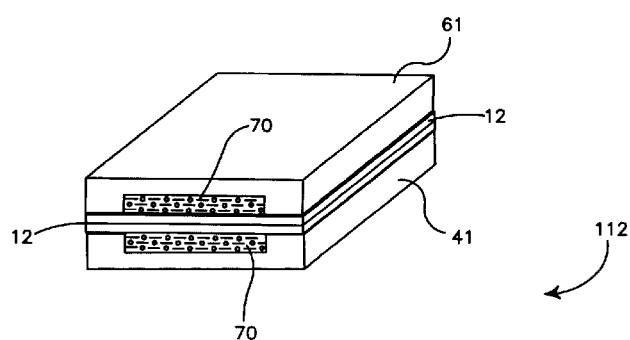

FIGS. 16(a) through 16(c) show a tenth embodiment of accelerometer assembly 112 of the present invention. FIG. 16(a) shows an exploded front top perspective view of the tenth embodiment. FIG. 16(c) shows a front top perspective view of the tenth embodiment. FIG. 16(b) shows a front end view of the tenth embodiment shown in FIG. 16(c). In FIGS. 16(a) through 16(c), stops 70 comprise a suitable viscoelastic damping fluid or gel disposed within the internal cavity defined by upwardly and downwardly extending arms 42 and 62 of upper and lower housing members 41 and 61 and accelerometer 12. FIGS. 16(a) through 16(c) do not show the covers or lids that would be required to be placed on the front and rear ends of assembly 112 to retain the damping fluid or gel within the cavity.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Although specific embodiments of the invention have been set forth herein in some detail, it is to be understood that this has been done for the purposes of illustration only, and is not to be taken as a limitation on the scope of the invention as defined in the appended claims. It is to be understood that various alterations, substitutions, and modifications may be made to the embodiment described herein without departing from the spirit and scope of the appended claims.

We claim:

1. An implantable stimulator comprising a pulse generator, an accelerometer assembly mounted within the stimulator for providing a signal indicative of a patient's level of activity, and control means responsive to the accelerometer signal for controlling operation of said pulse generator, the accelerometer assembly comprising:
   at least one of an upper housing member and a lower housing member, the upper member having at least one downwardly facing bottom surface, the lower member having at least one upwardly facing top surface;
   a sheet of piezoelectric material disposed generally within an imaginary plane defined by two major substantially horizontal orthogonal axes, the sheet having upper and lower surfaces, the sheet having formed therein a beam disposed along an imaginary longitudinal axis extending between the first and second ends, laterally extending outer members being formed in the sheet and adjacent at least the first end, the second end of the beam being deflectable along an imaginary vertical axis oriented substantially perpendicular to the plane;
   at least portions of the lower or upper surfaces of the first end of the sheet and optionally at least portions of the upper or lower surfaces of the laterally extending outer members of the sheet being attached to at least one of the upper surface of the lower housing member and the lower surface of the upper housing member, and
   at least one stop disposed at a location above or below the second end of the beam, the stop limiting the vertical range of motion through which the beam may deflect along the imaginary vertical axis to prevent failure, breakage or fracturing of the beam.

2. The stimulator of claim 1, wherein the sheet assumes a generally rectangular structural configuration.

3. The stimulator of claim 1, wherein the sheet has first and second generally parallel cuts disposed through the sheet, each cut extending in a longitudinal direction from the second end towards the first end and defining an edge of the beam.

4. The stimulator of claim 1, wherein the stop forms a rail disposed on at least one of the upper surface and the lower surface, respectively, of the upper housing member and the lower housing member, the stop further being disposed in a direction parallel to the imaginary longitudinal axis.

5. The stimulator of claim 4, wherein the rail is centrally disposed along the upper surface or the lower surface, respectively, of the upper or lower housing members.

6. The stimulator of claim 4, wherein the rail is a wide rail.

7. The stimulator of claim 1, wherein the stop forms a post or protrusion protruding from and disposed on one of the upper surface and the lower surface, respectively, of the upper housing member and the lower housing member.

8. The stimulator of claim 1, wherein the stop forms a rail disposed on at least one of the upper surface and the lower surface, respectively, of the upper housing member and the lower housing member, the stop further being disposed in a direction perpendicular to the imaginary longitudinal axis.

9. The stimulator of claim 1, wherein the stop forms a T-shaped rail disposed on at least one of the upper surface and the lower surface, respectively, of the upper housing member and the lower housing member.

10. The stimulator of claim 1, wherein the stop forms a dab or blob of silicone disposed on at least one of the upper surface and the lower surface, respectively, of the upper housing member and the lower housing member.

11. The stimulator of claim 1, wherein the upper and lower members are formed of a material selected from the group consisting of a nickel-cobalt-iron alloy, copper, brass, aluminum, nickel, a noble metal, a carbon composite, a ceramic composition and a plastic.

12. The stimulator of claim 1, wherein the upper and lower members are plated with an electrically conductive metal or alloy.

13. The stimulator of claim 1, wherein the sheet of piezoelectric material is formed from at least one of lead zirconate titanate, quartz, lithium niobate, and lithium titanate.

14. The stimulator of claim 1, wherein the upper or lower housing members are attached to sheet of piezoelectric material by at least one of electrically conductive thermoplastic, epoxy and glue.

15. An implantable stimulator comprising a pulse generator, an accelerometer assembly mounted within the stimulator for providing a signal indicative of a patient's level of activity, and control means responsive to said accelerometer signal for controlling operation of said pulse generator, the accelerometer assembly comprising:
   at least one of an upper housing member and a lower housing member, the upper member having at least one downwardly facing bottom surface, the lower member having at least one upwardly facing top surface;
   a sheet of piezoelectric material disposed generally within an imaginary plane defined by two major substantially horizontal orthogonal axes, the sheet having upper and lower surfaces, the sheet having formed therein a beam disposed along an imaginary longitudinal axis extending between the first and second ends, laterally extending outer members being formed in the sheet and adjacent at least the first end, the second end of the beam being deflectable along an imaginary vertical axis oriented substantially perpendicular to the plane;
   at least portions of the lower or upper surfaces of the first end of the sheet and optionally at least portions of the upper or lower surfaces of the laterally extending outer members of the sheet being attached to at least one of the upper surface of the lower housing member and the lower surface of the upper housing member, and
   at least one stop disposed on at least one of the upper surface of the beam and the lower surface of the beam, the stop limiting the vertical range of motion through which the beam may deflect along the imaginary vertical axis to prevent failure, breakage or fracturing of the beam.

16. The stimulator of claim 15, wherein the stop is formed of foam tape.

17. An implantable stimulator comprising a pulse generator, an accelerometer assembly mounted within the stimulator for providing a signal indicative of a patient's level of activity, and control means responsive to said accelerometer signal for controlling operation of said pulse generator, the accelerometer assembly comprising:

- at least one of an upper housing member and a lower housing member, the upper member having at least one downwardly facing bottom surface, the lower member having at least one upwardly facing top surface, the downwardly facing bottom surface and upwardly facing top surface defining at least portions of an internal cavity;
- a sheet of piezoelectric material disposed generally within an imaginary plane defined by two major substantially horizontal orthogonal axes, the sheet having upper and lower surfaces, the sheet having formed therein a beam disposed along an imaginary longitudinal axis extending between the first and second ends, laterally extending outer members being formed in the sheet and adjacent at least the first end, the second end of the beam being deflectable along an imaginary vertical axis oriented substantially perpendicular to the plane;
- at least portions of the lower or upper surfaces of the first end of the sheet and optionally at least portions of the upper or lower surfaces of the laterally extending outer members of the sheet being attached to at least one of the upper surface of the lower housing member and the lower surface of the upper housing member, and
- a stop comprising a visco-elastic damping fluid or gel disposed within the internal cavity, the stop limiting the vertical range of motion through which the beam may deflect along the imaginary vertical axis to prevent failure, breakage or fracturing of the beam.

18. The stimulator of claim 17, wherein the accelerometer assembly further comprises front and rear ends and correspondingly configured front and rear covers disposed on and in sealing engagement with the front and rear ends, the front and rear covers retaining the damping fluid or gel within the internal cavity.

19. A method of making an implantable stimulator comprising a pulse generator, an accelerometer assembly mounted within the stimulator for providing a signal indicative of a patient's level of activity, and control means responsive to the accelerometer signal for controlling operation of said pulse generator, the accelerometer assembly comprising at least one of an upper housing member and a lower housing member, the upper member having at least one downwardly facing bottom surface, the lower member having at least one upwardly facing top surface; a sheet of piezoelectric material disposed generally within an imaginary plane defined by two major substantially horizontal orthogonal axes, the sheet having upper and lower surfaces, the sheet having formed therein a beam disposed along an imaginary longitudinal axis extending between the first and second ends, laterally extending outer members being formed in the sheet and adjacent at least the first end, the second end of the beam being deflectable along an imaginary vertical axis oriented substantially perpendicular to the plane; at least portions of the lower or upper surfaces of the first end of the sheet and optionally at least portions of the upper or lower surfaces of the laterally extending outer members of the sheet being attached to at least one of the upper surface of the lower housing member and the lower surface of the upper housing member, and at least one stop disposed at a location above or below the second end of the beam, the stop limiting the vertical range of motion through which the beam may deflect along the imaginary vertical axis to prevent failure, breakage or fracturing of the beam, the method comprising the steps of:

(a) providing at least one of the upper housing member and the lower housing member;

(b) providing the sheet of piezoelectric material;

(c) forming the beam by cutting first and second notches in the sheet, the notches defining the lateral edges of the beam separating the beam from the laterally extending outer members;

(d) attaching at least portions of the lower or upper surfaces of the first end of the sheet and optionally at least portions of the upper or lower surfaces of the laterally extending outer members of the sheet to at least one of the upper surface of the lower housing member and the lower surface of the upper housing member, and (e) providing at least one stop at a location above or below the second end of the beam, the stop limiting the vertical range of motion through which the beam may deflect along the imaginary vertical axis to prevent failure or fracturing of the beam.

* * * * *

UNITED STATES PATENT AND TRADEMARK OFFICE
CERTIFICATE OF CORRECTION

PATENT NO. : 5,885,471

DATED : March 23, 1999

INVENTOR(S) : David A. Ruben; Mark E. Henschel; Lary R. Larson; Roy I. Inman; Louis Louis A. Molinari; Joan A. O'Gara; Ronald F. Messer It is certified that error appears in the above-identified patent and that said Letters Patent is hereby corrected as shown below: On the title page, item [75]:

Inventors: "Larry R. Larson" should be "Lary R. Larson"

Signed and Sealed this

Twenty-first Day of November, 2000

Attest:

Q. TODD DICKINSON

*Attesting Officer*      *Director of Patents and Trademarks*